(12) United States Patent
Jiang et al.

(10) Patent No.: US 10,633,686 B2
(45) Date of Patent: Apr. 28, 2020

(54) BIO-ENZYME SENSOR CAPABLE OF SUPER HYDROPHOBIC SOLID-LIQUID-GAS THREE-PHASE COEXISTENCE AND METHOD FOR PREPARING SAME

(71) Applicant: SUZHOU INSTITUTE OF NANO-TECH AND NANO-BIONICS (SINANO), CHINESE ACADEMY OF SCIENCES, SIP Suzhou, Jiangsu (CN)

(72) Inventors: Lei Jiang, Suzhou (CN); Xiangcheng Zhang, Suzhou (CN); Yongjiu Lei, Suzhou (CN); Ruize Sun, Suzhou (CN); Xinjian Feng, Suzhou (CN)

(73) Assignee: SUZHOU INSTITUTE OF NANO-TECH AND NANO-BIONICS (SINANO), CHINESE ACADEMY OF SCIENCES, Suzhou, Jiangsu (CN)

( * ) Notice: Subject to any disclaimer, the term of this patent is extended or adjusted under 35 U.S.C. 154(b) by 367 days.

(21) Appl. No.: 15/102,041

(22) PCT Filed: Mar. 7, 2014

(86) PCT No.: PCT/CN2014/073077
§ 371 (c)(1),
(2) Date: Jun. 6, 2016

(87) PCT Pub. No.: WO2015/081639
PCT Pub. Date: Jun. 11, 2015

(65) Prior Publication Data
US 2016/0304929 A1    Oct. 20, 2016

(30) Foreign Application Priority Data
Dec. 5, 2013   (CN) .......................... 2013 1 0652652

(51) Int. Cl.
*G01N 27/327* (2006.01)
*C12Q 1/00* (2006.01)

(52) U.S. Cl.
CPC ............. *C12Q 1/006* (2013.01); *C12Q 1/004* (2013.01); *C12Q 1/005* (2013.01); *G01N 27/3271* (2013.01)

(58) Field of Classification Search
CPC ........ C12Q 1/006; C12Q 1/004; C12Q 1/005; G01N 27/3271
See application file for complete search history.

(56) References Cited

FOREIGN PATENT DOCUMENTS

| CN | 101128599 | 2/2008 |
|---|---|---|
| CN | 101178373 | 5/2008 |

(Continued)

OTHER PUBLICATIONS

R. Garjonyte, et al. "Glucose biosensor based on glucose oxidase immobilized in electropolymerized polypyrrole and poly(0-phenylenediamine) films on a Prussian blue-modified electrode" Sensors and Actuators, B, 63(1-2): p. 122-128, Apr. (Year: 2000).*

(Continued)

*Primary Examiner* — J. Christopher Ball
(74) *Attorney, Agent, or Firm* — Hamre, Schumann, Mueller & Larson, P.C.

(57) ABSTRACT

A bio-enzyme sensor capable of super-hydrophobic solid-liquid-gas three-phase coexistence and a method for preparing the same. The bio-enzyme sensor comprises, from bottom to top, a base material with super-hydrophobic surface, a catalytic material having the function of catalyzing hydrogen peroxide, and bio-enzyme capable of reacting with a substance to be tested to generate hydrogen peroxide. A sufficient amount of oxygen can be provided for enzy- (Continued)

matic reaction by forming a state of solid-liquid-gas three-phase coexistence on the surface of the super-hydrophobic material.

16 Claims, 2 Drawing Sheets

(56) References Cited

FOREIGN PATENT DOCUMENTS

| | | |
|---|---|---|
| CN | 101530328 | 9/2009 |
| CN | 102011153 | 4/2011 |
| CN | 102352547 | 2/2012 |
| CN | 102755951 | 10/2012 |
| CN | 102815052 | 12/2012 |
| CN | 103101908 | 5/2013 |
| CN | 103386396 | 11/2013 |
| WO | 01/64938 | 9/2001 |

OTHER PUBLICATIONS

L. Xu, et al. "Reversible conversion of conducting polymer films from superhydrophobic to superhydrophilic" Angewandte Chemie International Edition, 44(37): p. 6009-6012, Sep. (Year: 2005).*

N. German, et al. "Glucose biosensor based on glucose oxidase and gold nanoparticles of different sizes covered by polypyrrole layer" Colloids and Surfaces, A, 413: p. 224-230, Nov. (Year: 2012).*

S. Yang, et al. "Microfabricated glucose biosensor with glucose oxidase entrapped in sol-gel matrix". Talanta 47(3): p. 735-743, Nov. (Year: 1998).*

C. Luo, et al. "Flexible Carbon Nanotube—Polymer Composite Films with High Conductivity and Superhydrophobicity Made by Solution Process", Nano Letters, 8(12): p. 4454-4458, Nov. (Year: 2008).*

J. Wang "Carbon-Nanotube Based Electrochemical Biosensors: A Review", Electroanalysis, 17(1): p. 7-14, Jan. (Year: 2005).*

S.H. Lim, et al. "A glucose biosensor based on electrodeposition of palladium nanoparticles and glucose oxidase onto Nafion-solubilized carbon nanotube electrode", Biosensors and Bioelectronics, 20(11): p. 2341-2346, May (Year: 2005).*

L.C. Clark, Jr., and C. Lyons, "Electrode Systems for Continuous Monitoring in Cardiovascular Surgery," Annals of the New York Academy of Sciences, (1962) vol. 102, p. 29-45. (citation on p. 1 of Specification).

International Search Report for international application No. PCT/CN2014/073077, dated Sep. 11, 2014, 4 pages.

* cited by examiner

BIO-ENZYME SENSOR CAPABLE OF SUPER HYDROPHOBIC SOLID-LIQUID-GAS THREE-PHASE COEXISTENCE AND METHOD FOR PREPARING SAME

TECHNICAL FIELD

The present invention relates to an enzyme biosensor and the preparation method thereof, and particularly to an enzyme biosensor based on superhydrophobic substrate with solid-liquid-gas three-phase coexistence and the method for preparation.

BACKGROUND

Since Leland Clark first proposed a theoretical model wherein the enzyme electrode was used to measure glucose in 1962 (Ref 1: Clark, L. C.; Jr.; Lyons, C. Electrode systems for continuous monitoring in cardiovascular surgery. *Ann. N. Y. Acad. Sci.* 1962, 102, 29-45), researchers have never stopped the study on glucose sensor. The basic model by Clark comprises the following three elements: an oxygen electrode, an oxygen semi-permeable membrane and glucose enzyme, wherein the enzyme is immobilized on the electrode (also referred to as an enzyme electrode). The detection principle is to measure reduction of oxygen concentration in blood and then to calculate glucose concentration, i.e., glucose is oxidized to produce hydrogen peroxide under the action of glucose oxidase, thus consuming blood oxygen. Therefore, the glucose concentration can be obtained by calculating the concentration reduction of blood oxygen.

It was in 1975 that Clark's model was really and successfully converted into commodity as a Model 23A YSI Analyzer, which was a glucose analyzer produced by Yellow Springs Instrument Company. The analyzer is also a standard glucose analyzer which is still used in world now. This instrument can calculate the glucose concentration by measuring hydrogen peroxide ($H_2O_2$). The basic principle thereof is to measure glucose concentration based on change of blood oxygen concentration. All instruments, which are used for measuring blood glucose and developed based on Clark's model, are based on measurement of blood oxygen. The problem is that oxygen in the blood is very limited and in $\mu M$ magnitude. Compared with blood glucose in mM magnitude, such a low concentration is minimal. Therefore, for all instruments based on Clark's glucose model, blood must be diluted to a level that is at least equivalent to the level of oxygen in liquid before detection. However, the additional dilution step is not only cumbersome and time-consuming but also to introduce systematic errors which lead to inaccurate measurement results.

Hence, there is an urgent need in the art to develop a new detection method which can be used easily and can obtain accurate measurement results as well as corresponding detection tools.

SUMMARY OF THE INVENTION

The purpose of the present invention is to provide a detection method which can be used easily and can obtain accurate measurement results as well as corresponding detection tools.

In the first aspect of the present invention, a bio-enzyme sensor (or enzyme biosensor) capable of superhydrophobic solid-liquid-gas three-phase coexistence is provided, wherein the bio-enzyme sensor comprises:

(a) a substrate having superhydrophobic properties;
(b) a catalytic material having a catalytic function for hydrogen peroxide;
(c) a bio-enzyme capable of reacting with a substance to be detected to generate hydrogen peroxide, wherein, the catalytic material (b) is distributed on the substrate (a), or the substrate (a) itself has the catalytic material (b); and the bio-enzyme (c) is located on surface of the substrate (a) and/or the catalytic material (b).

In another preferred embodiment, the term "distributed on the substrate" includes "distributed on at least one major surface of the substrate", or "distributed on partial surface or all surface of the substrate".

In another preferred embodiment, at least a portion of the bio-enzyme (c) and at least a portion of the catalytic material (b) are in contact with each other.

In another preferred embodiment, the term "in contact with each other" includes both direct contact and indirect contact (i.e. hydrogen peroxide generated by the bio-enzyme can be passed to or spread to the catalytic material (b)).

In another preferred embodiment, when the sensor is in contact with a solution containing the substance to be detected, a "solid phase-liquid phase-gas phase" coexistence form is formed at the contact interface.

In another preferred embodiment, in the "solid phase-liquid phase-gas phase" coexistence form, the sensor acts as the solid phase, and the solution acts as the liquid phase, and air or atmospheric acts as the gas phase.

In another preferred embodiment, the contact between the sensor and the solution containing the substance to be detected includes a contact with the surface of the solution, and a portion of sensor or entire sensor is immersed into the solution.

In another preferred embodiment, when the sensor is applied to (or applied onto) a selected liquid system, the bio-enzyme and the catalytic material are at least distributed on the interface of the liquid phase covering the superhydrophobic structures and the oxygen-containing gas phase filling within the superhydrophobic structures, thus forming a solid-liquid-gas three-phase coexistence form.

In another preferred embodiment, the substrate has a superhydrophobic structure.

In another preferred embodiment, the superhydrophobic structure is a porous material.

In another preferred embodiment, the substrate is a conductive substrate.

In another preferred embodiment, the term "distributed on the substrate" refers to that a substance or material (e.g. catalytic material) is distributed on partial surface or all surface of the substrate.

In another preferred embodiment, the sensor is selected from the group consisting of:

(S1) a superhydrophobic solid-liquid-gas three-phase coexisted bio-enzyme sensor, wherein the sensor comprises:
the substrate having superhydrophobic properties, and the bio-enzyme as well as the catalytic material distributed on the substrate, wherein
the catalytic material has a catalytic function for hydrogen peroxide and the bio-enzyme is capable of reacting with the substance to be detected to generate hydrogen peroxide;

(S2) a superhydrophobic solid-liquid-gas three-phase coexisted bio-enzyme sensor, wherein the sensor comprises:
a conductive substrate having superhydrophobic properties, wherein the substrate itself comprises a catalytic material having a catalytic function for hydrogen peroxide, and the enzyme capable of reacting with the substance to be detected to generate hydrogen peroxide;

(S3) a superhydrophobic solid-liquid-gas three-phase coexisted bio-enzyme sensor, wherein the sensor comprises:

a conductive substrate having superhydrophobic structures, and the bio-enzyme and the catalytic material, wherein the bio-enzyme is capable of reacting with the substance to be detected to generate hydrogen peroxide and the catalytic material has a catalytic function for hydrogen peroxide;

and, when the surface of the superhydrophobic structure is applied with a selected liquid system, the bio-enzyme and the catalytic material are at least distributed on the interface of the liquid phase covering the superhydrophobic structures and the oxygen-containing gas phase filling within the superhydrophobic structures, thus forming a solid-liquid-gas three-phase coexistence form;

(S4) a superhydrophobic solid-liquid-gas three-phase coexisted bio-enzyme sensor, wherein the sensor comprises:

a conductive substrate having superhydrophobic structures, wherein the materials used for forming the superhydrophobic structures comprises a catalytic material having a catalytic function for hydrogen peroxide, and the bio-enzyme capable of reacting with the substance to be detected to generate hydrogen peroxide;

and, when the surface of the superhydrophobic structure is applied with a selected liquid system, the bio-enzyme and the catalytic material are at least distributed on the interface of the liquid phase covering the superhydrophobic structures and the oxygen-containing gas phase filling within the superhydrophobic structures, thus forming a solid-liquid-gas three-phase coexistence form.

In another preferred embodiment, the bio-enzyme sensor has one or more characteristics selected from the group consisting of:

(F1) when the substance to be detected has a concentration range of 1 μM-500 mM, and preferably 1 μM-150 mM, the measuring current of the sensor is linear or nearly linear (in the measuring range);

(F2) the response time of the sensor is ≤5 seconds, preferably ≤2 seconds, and more preferably ≤1 second;

(F3) operation of the sensor is not influenced by oxygen content in the solution to be detected.

In another preferred embodiment, the substrate comprises metal materials, carbon materials or high molecular porous materials;

wherein the metal materials comprise foamed nickel, foamed copper, foamed titanium, foamed aluminum and iron net, foamed copper mesh, foamed aluminum net, aluminum and iron mesh, copper mesh or aluminum mesh;

the carbon materials comprise graphene, carbon nanotube construct, carbon fiber, expanded graphite, photolithography graphite or porous carbon materials;

the high molecular porous materials comprise polyaniline membrane, polypyridine membrane or polypyrrole membrane.

In another preferred embodiment, the catalytic material comprises inorganic materials and/or organic materials;

wherein the inorganic materials comprise carbon materials, metals or metal oxides;

the metals include platinum, rhodium, ruthenium, gold, cobalt, iron or nickel;

the metal oxides include one oxide or a combination of two or more oxides, wherein the oxide is selected from rhodium, ruthenium, cobalt, iron or nickel;

the organic materials include biological materials or metal organic complexes, wherein the biological materials comprise cytochrome C, hydrogen peroxide oxidase or Prussian blue.

In another preferred embodiment, the catalytic material comprises metal and/or metal oxide nanoparticles.

In another preferred embodiment, the bio-enzyme includes glycerol kinase, α-glycerophosphate oxidase, cholesterol esterase, cholesterol dehydrogenase, cholesterol oxidase, glucose oxidase, glucose dehydrogenase, lactate dehydrogenase, malic dehydrogenase, bilirubin oxidase, ascorbic acid oxidase, peroxidase, uricase, collagenase, hyaluronic acid enzyme, proteases, proteolytic enzyme, or combinations thereof.

In another preferred embodiment, the bio-enzyme sensor further comprises a protective film, wherein the protective film is at least used to protect the bio-enzyme and to fix the bio-enzyme on surface of the substrate.

In another preferred embodiment, the protective film prevents the bio-enzyme from permeating through the protective film, but allows the following materials to permeate through: solvent molecules forming the selected liquid system and the substance to be detected.

In another preferred embodiment, the protective film covers the superhydrophobic structure.

In another preferred embodiment, the protective film is formed from materials selected from the group consisting of: chitosan, perfluorosulfonic acid proton membrane, and combinations thereof.

In the second aspect of the present invention, a method for preparing the superhydrophobic solid-liquid-gas three-phase coexisted bio-enzyme sensor of the first aspect of the present invention is provided, wherein the method comprises the following steps:

(i) providing a substrate (a) having superhydrophobic properties, wherein a catalytic material (b) is distributed on the substrate (a), or the substrate (a) itself has the catalytic material (b), wherein the catalytic material has a catalytic function for hydrogen peroxide; and (ii) loading bio-enzyme on the substrate (a) of step (i), thereby forming the superhydrophobic solid-liquid-gas three-phase coexisted bio-enzyme sensor of the first aspect of the present invention, wherein the bio-enzyme is capable of reacting with the substance to be detected to generate hydrogen peroxide.

In another preferred embodiment, the bio-enzyme (c) is located on the surface of the substrate (a) and/or the catalytic material (b).

Preferably, the preparation method comprises: providing a substrate having super hydrophobic properties, and fixing a catalytic material having a catalytic function for hydrogen peroxide and a bio-enzyme capable of reacting with the substance to be detected to generate hydrogen peroxide on the substrate.

Preferably, the preparation method comprises: providing a conductive substrate having superhydrophobic properties, wherein the substrate itself comprises a catalytic material having a catalytic function for hydrogen peroxide, and, fixing a bio-enzyme on the substrate, wherein the bio-enzyme is capable of reacting with the substance to be detected to generate hydrogen peroxide.

Preferably, the preparation method comprises: providing a conductive substrate wherein the surface of the substrate has superhydrophobic structures, and fixing on the superhydrophobic structures a catalytic material having a catalytic function for hydrogen peroxide and a bio-enzyme capable of reacting with the substance to be detected to generate hydrogen peroxide;

and, when the surface of the superhydrophobic structure is applied with a selected liquid system, the bio-enzyme and the catalytic material are at least distributed on the interface of the liquid phase covering the superhydrophobic structures and the oxygen-containing gas phase filling within the superhydrophobic structures, thus forming a solid-liquid-gas three-phase coexistence form.

Preferably, the preparation method comprises: providing a conductive substrate wherein the surface of the substrate has superhydrophobic structures, wherein the material used for forming the superhydrophobic structures comprises a catalytic material having a catalytic function for hydrogen peroxide;

and, fixing a bio-enzyme capable of reacting with the substance to be detected to generate hydrogen peroxide on the superhydrophobic structures;

and, when the surface of the superhydrophobic structure is applied with a selected liquid system, the bio-enzyme and the catalytic material are at least distributed on the interface of the liquid phase covering the superhydrophobic structures and the oxygen-containing gas phase filling within the superhydrophobic structures, thus forming a solid-liquid-gas three-phase coexistence form.

Preferably, the method further has one or more of the following characteristics:

(M1) in step (i), firstly providing a conductive substrate wherein the surface of the substrate has superhydrophobic structures or superhydrophobic properties, and then loading the catalytic material on the substrate;

(M2) in step (ii), the loading step comprises the following steps: applying the solution containing bio-enzyme onto the substrate and drying, so that the bio-enzyme is attached onto the surface of the substrate;

(M3) the catalytic material comprises inorganic materials and/or organic materials;

(M4) the bio-enzyme includes glycerol kinase, α-glycerophosphate oxidase, cholesterol esterase, cholesterol dehydrogenase, cholesterol oxidase, glucose oxidase, glucose dehydrogenase, lactate dehydrogenase, malic dehydrogenase, bilirubin oxidase, ascorbic acid oxidase, peroxidase, uricase, collagenase, hyaluronic acid enzyme, proteases or proteolytic enzyme;

(M5) the substrate is a conductive substrate whose surface is modified by a material having low surface energy.

In another preferred embodiment, the materials having low surface energy include fluorocarbon, fluorosilicone compound, silane coupling agent, long-chain alkyl compound, or combinations thereof.

Preferably, the inorganic materials comprise carbon materials, metals or metal oxides;

Preferably, the metals include platinum, rhodium, ruthenium, gold, cobalt, iron or nickel;

Preferably, the metal oxides include one oxide or a combination of two or more oxides, wherein the oxide is selected from rhodium, ruthenium, cobalt, iron or nickel;

Preferably, the organic materials include biological materials or metal organic complexes, wherein the biological materials comprise cytochrome C, hydrogen peroxide oxidase or Prussian blue.

Preferably, the catalytic material comprises metal and/or metal oxide nanoparticles.

Preferably, the method further comprises:

(iii) applying a film-forming material on the substrate loaded with the bio-enzyme and drying, thereby forming a protective film on the substrate.

In another preferred embodiment, the protective film is permeable to the following materials: solvent molecules forming the selected liquid system and the substance to be detected, but it can prevent the bio-enzyme from permeating through the protective film.

In another preferred embodiment, the film-forming materials comprise chitosan or perfluorosulfonic acid proton membrane.

In another preferred embodiment, in step (i), it comprises: providing a conductive substrate, and modifying the surface of the conductive substrate with materials having a low surface energy, thereby forming a conductive substrate having superhydrophobic properties.

In a specific embodiment, the preparation method may further comprise the following steps:

(1) providing a conductive substrate wherein the surface thereof has superhydrophobic structures;

(2) fixing the catalytic material on the superhydrophobic structures;

(3) applying a solution containing bio-enzyme to the superhydrophobic structures and drying at room temperature, so that the bio-enzyme is attached to the surface of the superhydrophobic structures.

As a more preferred embodiment, the preparation method may further comprise:

applying film-forming materials to the substrate which has loaded with the bio-enzyme, especially to the superhydrophobic structures, and drying at room temperature, thereby forming a protective film on the superhydrophobic structures, wherein the protective film is at least permeable to solvent molecules forming the selected liquid system and the substance to be detected, but it can prevent the bio-enzyme from permeating through the protective film.

As one of the specific embodiments, the preparation method may further comprise:

providing a conductive substrate and modifying the surface of the conductive substrate by materials having a low surface energy, thereby forming a conductive substrate whose surface has superhydrophobic structure.

Compared with the prior art, the present invention at least has the following advantages:

(1) It can always remain solid-gas-liquid three-phase coexisted state on the surface of superhydrophobic materials and supply oxygen required for enzyme-catalyzed reactions by air, which can fundamentally solve the problem of lacking oxygen for enzyme-catalyzed biological reaction, and give the sensor the following characteristics: a wide detection range, a low detection limit, fast response time, accurate detection results and so on.

(2) The superhydrophobic materials employed in the bio-enzyme sensor of the present invention have low cost, is simple to prepare, have no severe temperature, pressure, equipment, or requirements, and is easy to mass production.

(3) The enzyme biosensor of the present invention is convenient to apply, and can be long-term used and has good stability.

(4) The materials used in the enzyme biosensor of the present invention are all biocompatible materials which are harmless to organism, especially suitable for continuous detection in human body.

(5) The detection method of the present invention is simple and does not require additional dilution step. In the prior art, the liquid to be detected must be diluted before carrying out blood glucose detection. Without dilution and/or centrifugation, the enzyme biosensor of the present invention can detect the substance to be detected in-situ and in real-time, so that it not only has the reduced time-consuming but also can significantly increase the detection accuracy and reduce measurement errors.

(6) The bio-enzyme sensor of the present invention is suitable for clinical testing and outdoor detection and other occasions, and does not need large-scale equipments (such as centrifuges) involved in traditional blood glucose testing method or standard dilution agents.

DETAILED DESCRIPTION OF INVENTION

Through extensive and intensive long research, for the first time, the inventors have developed a (super) hydrophobic bio-enzyme sensor which has a solid-liquid-gas three-phase coexistence state at work. When using the sensor of the invention, it can always remain solid-gas-liquid three-phase coexistence state on the surface of superhydrophobic materials and supply oxygen required for enzyme-catalyzed reactions by air, thereby significantly increasing the detection range of the sensor, and it has fast response time as well as accurate detection results. Based on this, the present invention is completed.

Terms

As used herein, the terms "superhydrophobic solid-liquid-gas three-phase coexisted bio-enzyme sensor", "the sensor of the present invention", "the bio-enzyme sensor of the present invention" can be used interchangeably and refer to a bio-enzyme sensor having superhydrophobic properties, which has a solid-liquid-gas three-phase coexisted state(or phenomenon) at work.

As used herein, the terms "superhydrophobic", "superhydrophobic properties" can be used interchangeably and refer to that an object (e.g., bio-enzyme sensors) or a material (e.g. substrate) has excellent hydrophobic properties. The hydrophobic properties can be determined and characterized by conventional methods. Typically, at normal temperature and pressure detection conditions, when the contact angle is greater than or equal to 120 degrees (preferably) 150°, the substance can be considered excellent in hydrophobic or superhydrophobic.

As used herein, room temperature refers to the ambient temperature, typically 0-50° C., preferably 4-30° C.

Bio-Enzyme Sensor

One aspect of the present invention is to provide a superhydrophobic solid-liquid-gas three-phase coexisted bio-enzyme sensor, which can provide a sufficient supply of oxygen to enzymatic reaction by forming a solid-liquid-gas three-phase coexisted structure on the surface of the superhydrophobic materials, thereby effectively improving the performance of bio-enzyme sensors (such as detection range and detection limit).

Figure 1:
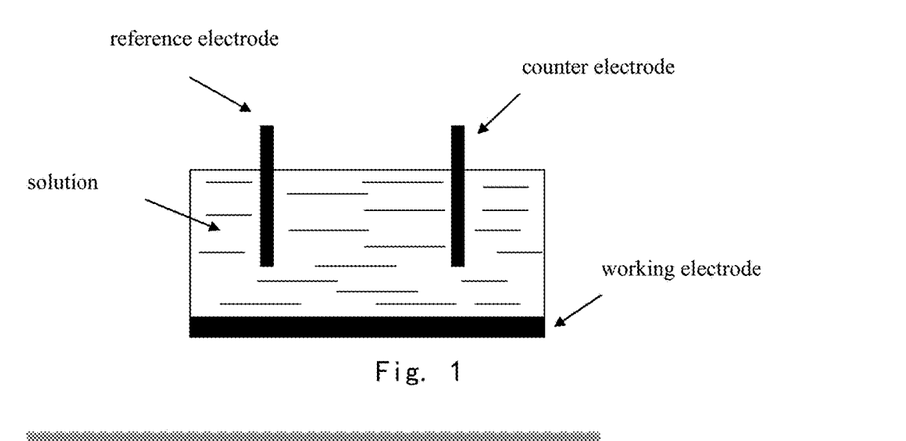
FIG. 1 is a schematic diagram of application state of a superhydrophobic solid-liquid-gas three-phase coexisted bio-enzyme sensor in an embodiment of the present invention.

Referring to FIG. 1, in application, the superhydrophobic solid-liquid-gas three-phase coexisted bio-enzyme sensor of the present invention can be used as a working electrode and combined with a reference electrode needed for electrochemistry or combined with a reference electrode as well as a counter electrode at the same time, together with the corresponding conductive medium, which then can be used for analysis and detection, such as calibration or detection of glucose.

A superhydrophobic solid-liquid-gas three-phase coexisted bio-enzyme sensor of the present invention may comprise:

a conductive substrate having superhydrophobic structures, and a bio-enzyme and a catalytic material, wherein the bio-enzyme is capable of reacting with the substance to be detected to generate hydrogen peroxide and the catalytic material has a catalytic function for hydrogen peroxide.

Further, as one preferred embodiment, the sensor may further comprise a protective film, wherein the protective film is at least used to protect the bio-enzyme and to fix the bio-enzyme on the surface of the superhydrophobic structures.

Figure 2:
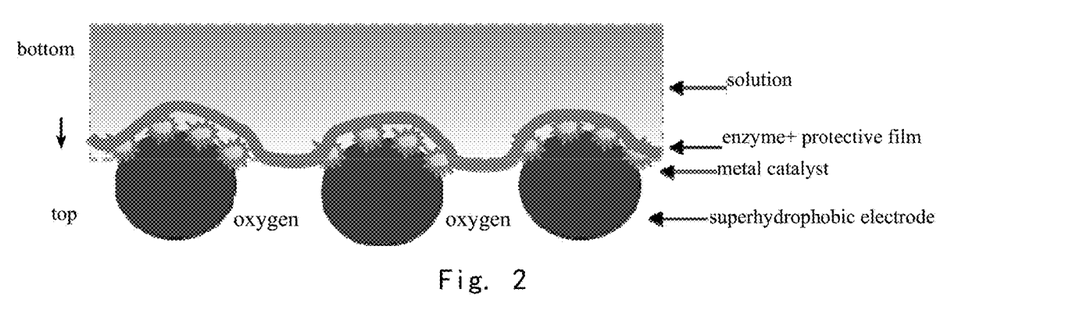
FIG. 2 is a structure schematic drawing of a superhydrophobic solid-liquid-gas three-phase coexisted bio-enzyme sensor in an embodiment of the present invention.

More specifically, referring to FIG. 2, the protective film covers the superhydrophobic structures (superhydrophobic electrode), which is at least permeable to solvent molecules in the selected liquid system and the substance to be detected, but can prevent the bio-enzyme.

A superhydrophobic solid-liquid-gas three-phase coexisted bio-enzyme sensor of the present invention may comprise:

a substrate having superhydrophobic properties, and a bio-enzyme as well as a catalytic material distributed on the substrate, wherein the catalytic material has a catalytic function for hydrogen peroxide and the bio-enzyme is capable of reacting with the substance to be detected to generate hydrogen peroxide.

Another superhydrophobic solid-liquid-gas three-phase coexisted bio-enzyme sensor of the present invention may comprise:

a conductive substrate having superhydrophobic properties, wherein the substrate itself comprises a catalytic material having a catalytic function for hydrogen peroxide, and a bio-enzyme capable of reacting with the substance to be detected to generate hydrogen peroxide.

Another superhydrophobic solid-liquid-gas three-phase coexisted bio-enzyme sensor of the present invention may comprise:

a conductive substrate having superhydrophobic structures, and a bio-enzyme and a catalytic material, wherein the bio-enzyme is capable of reacting with the substance to be detected to generate hydrogen peroxide and the catalytic material has a catalytic function for hydrogen peroxide;

and, when the surface of the superhydrophobic structure is applied with a selected liquid system, the bio-enzyme and the catalytic material are at least distributed on the interface of the liquid phase covering the superhydrophobic structures and the oxygen-containing gas phase filling within the superhydrophobic structures, thus forming a solid-liquid-gas three-phase coexistence form.

Another superhydrophobic solid-liquid-gas three-phase coexisted bio-enzyme sensor of the present invention may comprise:

a conductive substrate having superhydrophobic structures, wherein the materials used for forming the superhydrophobic structures comprises a catalytic material having a catalytic function for hydrogen peroxide, and a bio-enzyme capable of reacting with the substance to be detected to generate hydrogen peroxide;

and, when the surface of the superhydrophobic structure is applied with a selected liquid system, the bio-enzyme and the catalytic material are at least distributed on the interface of the liquid phase covering the superhydrophobic structures and the oxygen-containing gas phase filling within the superhydrophobic structures, thus forming a solid-liquid-gas three-phase coexistence form.

Substrate

For the conductive substrate of the present invention, which can be selected from a conductive material whose surface has superhydrophobic properties after superhydrophobic treatment or a conductive material having superhydrophobic surface itself, such materials can be obtained via various ways such as in market or self-made.

For example, for a conductive material whose surface has superhydrophobic properties after superhydrophobic treatment, it can be obtained by modifying it with materials having a low surface energy. Such materials having a low surface energy include (but are not limited to): fluorocarbon, fluorosilicone compound, silane coupling agent or long-chain alkyl compound etc., or can be particles having a low surface energy etc., including but not limited to polytetrafluoroethylene micropowder, FEP micropowder etc. While the corresponding modification method can refer to CN102815052A, CN 102011153A and other documents.

The conductive substrate may select superhydrophobic conductive materials, including (but not limited to) metal materials, carbon materials or high molecular porous materials or the like. For example, the metal materials include (but not limited to): foamed nickel, foamed copper, foamed titanium, foamed aluminum and iron net, foamed copper mesh, foamed aluminum net, aluminum and iron mesh, copper mesh or aluminum mesh, while the carbon materials include (but not limited to): graphene, carbon nanotube construct, carbon fiber, expanded graphite, photolithography graphite, porous carbon materials etc., and the high molecular porous materials include (but not limited to): polyaniline membrane, polypyridine membrane or polypyrrole membrane etc.

Catalytic Materials

The foregoing catalytic materials refer to materials capable of catalyzing hydrogen peroxide for electrochemical reaction, and the materials include inorganic, biological, metal and metal oxide materials. For example, it can be selected from carbon nanotube, graphene, cytochrome C, hydrogen peroxide oxidase, Prussian blue, platinum (Pt), rhodium (Rh), ruthenium (Ru), gold (Au), cobalt (Co) oxide, iron (Fe) oxide, nickel (Ni) oxide etc. There is no limitation to the form thereof.

In the present invention, the catalytic material may comprise inorganic materials and/or organic materials;

wherein the inorganic materials may comprise carbon and/or metals and/or compounds containing metal element;

the organic materials include (but are not limited to): biological materials and/or metal organic complexes; for example, the biological materials can be selected from (but are not limited to): cytochrome C, hydrogen peroxide oxidase or Prussian blue etc.

The metals include (but are not limited to): platinum, rhodium, ruthenium, gold, cobalt, iron or nickel.

As one of the more preferred embodiments, the catalytic materials include (but are not limited to) metals and/or metal oxide nanoparticles.

Bio-Enzyme

As used herein, the bio-enzyme can be selected from any active enzyme capable of oxidizing the substance to be detected (e.g., glucose) and generating hydrogen peroxide. For example, it includes (but is not limited to): glycerol kinase, α-glycerophosphate oxidase, cholesterol esterase, cholesterol dehydrogenase, cholesterol oxidase, glucose oxidase, glucose dehydrogenase, lactate dehydrogenase, malic dehydrogenase, bilirubin oxidase, ascorbic acid oxidase, peroxidase, uricase, collagenase, hyaluronic acid enzyme, proteases, proteolytic enzyme, or combinations thereof.

Film-Forming Materials

As used herein, a film-forming material refers to a compound which can form a film on the surface of materials and serve to protect and fix the enzyme molecule. It includes but is not limited to chitosan and perfluorosulfonic acid proton membrane (Nafion). It can also be any conventional material which can be used to constitute semi-permeable membrane or permeable membrane, wherein the semi-permeable membrane or permeable membrane can prevent biological material from permeating but allowing small molecules or ions to permeate. For example, materials commonly used in the preparation include cuprammonium regenerated cellulose, cellulose acetate, polyacrylonitrile, ethylene-vinyl alcohol copolymer and polymethyl methacrylate, polysulfone, polyacrylamide and the like.

In addition, in one embodiment of the present invention, for the conductive substrate itself having the aforementioned catalytic properties, especially the conductive substrate whose superhydrophobic structures comprise a catalytic material having a catalytic function for hydrogen peroxide, the preceding operation to load catalytic materials on superhydrophobic structures can also be omitted.

The Preparation Method of the Bio-Enzyme Sensor

Another aspect of the present invention provides a method for preparing the superhydrophobic solid-liquid-gas three-phase coexisted bio-enzyme sensor, wherein the method comprises: providing a conductive substrate having superhydrophobic structures, and fixing or loading a catalytic material having a catalytic function for hydrogen peroxide and a bio-enzyme capable of reacting with the substance to be detected to generate hydrogen peroxide on the superhydrophobic structures.

Further, when the surface of the superhydrophobic structure is applied with a selected liquid system, the bio-enzyme and the catalytic material are at least distributed on the interface of the liquid phase covering the superhydrophobic structures and the oxygen-containing gas phase filling within the superhydrophobic structures, thus forming a solid-liquid-gas three-phase coexistence form.

The aforementioned "selected liquid system" refers to water or an aqueous solution containing at least the substance to be detected and the like, and it also can be blood or other physiological liquids etc.

The foregoing "substance to be detected" refers to a substance which can be oxidized by the bio-enzyme and generate hydrogen peroxide, including glucose etc., but is not limited thereto.

The aforementioned "oxygen-containing gas phase" includes air or gases formed by oxygen and other auxiliary gases (e.g., an inactive gas such as nitrogen and inert gas such as argon).

In one particular embodiment, the preparation method specifically comprises the following steps:

(1) providing a conductive substrate having superhydrophobic structures;

(2) fixing the catalytic material on the superhydrophobic structures;

(3) applying a solution containing bio-enzyme to the superhydrophobic structures and drying at room temperature, so that the bio-enzyme is attached to the surface of the superhydrophobic structures.

As one of the more preferred embodiments, the preparation method may further comprise:

applying a film-forming material to the superhydrophobic structures loaded with the bio-enzyme, and drying at room temperature, thereby forming a protective film on the superhydrophobic structures, wherein the protective film is at least permeable to solvent molecules forming the selected liquid system and the substance to be detected, but it can prevent the bio-enzyme from permeating through the protective film.

In one particular embodiment, the method for preparing the aforementioned sensor can comprise the following steps, including: preparing a superhydrophobic material; treating surface with a metal or metal oxide material; adding a bio-enzyme solution onto the treated surface; and using a film-forming material to form a film for protection.

A preferred preparation process is as follows:

(1) Preparation of superhydrophobic materials

For the conductive substrate itself having superhydrophobic function, it does not need further hydrophobic treatment. As for hydrophilic material itself, it can be modified by a substance having a low surface energy. For example, it can be placed in an ethanol solution of silicon fluoride to soak for 3-24 hrs, and then it is taken out to clean residual materials from the surface with ethanol, and the treated sample is finally heated to polymerize at 100° C. for 2 h in oven, to obtain superhydrophobic electrode material (i.e., the aforementioned conductive substrate, or superhydrophobic materials).

(2) Modification with metal or metal oxide materials

The superhydrophobic materials obtained in above step (1) are fixed in an electrode pool, and a solution relevant to catalytic material for loading is added into the electrode pool. Taking Pt for example, in order to deposit Pt metal on the surface of the superhydrophobic materials, chloroplatinic acid solution (10 g/L $H_2PtCl_6$, the concentration ratio of $H_2PtCl_6$:1M $H_2SO_4$:$H_2O$=13:25:12) is added into the electrode pool. The treated superhydrophobic material is used as a working electrode, and a platinum wire electrode is added as a counter electrode, and Ag/AgCl electrode is used as a reference electrode. Use instant current method, electro-deposition is conducted for 150-500 s in a potential of 0-0.5 V.

(3) Loading Bio-enzyme

The above prepared superhydrophobic materials which are treated with metal and/or metal oxide materials are continuously fixed in electrode pool. A solution containing the bio-enzyme is added dropwise on the surface of the superhydrophobic materials, e.g., an aqueous solution of glucose oxidase (wherein an enzyme-containing amount may be 0.1-20U, wherein U is enzyme activity unit). Then, the hydrophobic materials are placed for drying at room temperature. The dried superhydrophobic materials are loaded with bio-enzyme, and the bio-enzyme has reactivity.

(4) Forming a Film for Protection

A protective film is used to protect the surface of the above superhydrophobic materials loaded with bio-enzyme, thus preventing the bio-enzyme molecules loaded on the surface of the superhydrophobic materials from dissolving or falling off. The operation method may be: applying a certain amount of film-forming substances on the surface of above dried superhydrophobic materials, and then the superhydrophobic materials are placed for drying at room temperature. The dried superhydrophobic materials have a layer of film formed by film-forming substances on the surface thereof, so that when the superhydrophobic material is applied with an aqueous solution, the bio-enzyme molecules will not be dissolved in the solution.

Taking chitosan as a representative film-forming substance, on the surface of above superhydrophobic materials loaded with bio-enzyme, a 10 μL chitosan solution is added dropwise, wherein the content of chitosan may be 1 mg-250 mg. Then, the superhydrophobic materials are placed for drying naturally at room temperature. Chitosan film can be obviously observed on the surface of the dried superhydrophobic materials.

Further, the above steps (3) and (4) may be combined in one step, i.e. blending the bio-enzyme and the protective membrane material and forming a film together.

In the present invention, the superhydrophobic materials treated with metal and/or metal oxide materials and prepared in the above step (2) can be fixed in the electrode pool, and a mixed solution containing bio-enzyme and film-forming protective materials is added (e.g. dropwise) on the surface of superhydrophobic materials, such as a solution of glucose oxidase and film-forming substance (such as chitosan). Typically, the solution can be made by mixing an enzyme-containing aqueous solution with a solution containing a film-forming material There is no particular limitation on mixing ratio of two substances, as long as the protective film can be formed, and the mixing ratio usually is 1:50-50:1, preferably 1:10-10:1, and more preferably 2:1 to 1:2. In the solution, the content of the enzyme and the film-forming material can be determined depending on the kinds of the materials, as long as the protective film having a certain amount of enzyme can be formed on the surface. Typically, for a surface of 1-4 $cm^2$, the amount of enzyme in the protective film is usually 0.1-20U (U is enzyme activity unit), while the content of film-forming material (such as chitosan) is generally 1 mg-250 mg.

Subsequently, the superhydrophobic materials are dried (e.g. naturally drying at room temperature).

In the present invention, the bio-enzyme on the surface of the dried superhydrophobic materials is reactive. In addition, when the superhydrophobic materials are placed into an aqueous solution, the bio-enzyme molecules can be protected by the film-forming substance, so that it will not dissolve in the solution.

Industrial Applicability and Advantages

Compared with the conventional enzyme biosensor, the enzyme biosensor based on the superhydrophobic electrode in the present invention has advantages of high accuracy, wide detection range, a low detection limit, high sensitivity, short response time and so on.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacture's instructions. Unless indicated otherwise, parts and percentage are calculated by weight.

The electrochemical process and measurement in the following examples were conducted by CHI-660E electrochemical workstation produced by Shanghai Chen Hua Instrument Co., Ltd. While the solvents such as ethanol and the like and experimental substrates and reagents such as glucose and the like used in the following examples were purchased from Sigma-Aldrich Corporation, and glucose oxidase reagents was purchased from Sigma-Aldrich Corporation or Asahi Kasei Corporation, there are no limitation.

EXAMPLE 1 Preparation of Superhydrophobic Glucose Sensor (1) A piece of superhydrophobic carbon fiber paper with a certain area (approximate 1 cm×1 cm square) was placed into ethanol, and ultrasonically cleaned for 1 min. After cleaning, the carbon fiber paper was taken out and placed to dry naturally.

Figure 3:
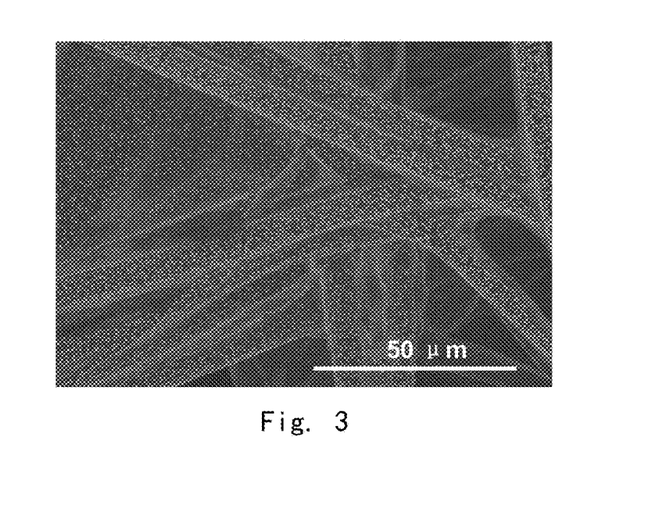
FIG. 3 is a SEM photograph of carbon fiber paper after depositing Pt metal in Example 1 in the present invention.

(2) The materials obtained in step (1) were fixed in an electrochemical working pool. A chloroplatinic acid solution (10 g/L $H_2PtCl_6$, the concentration ratio of $H_2PtCl_6$: 1M $H_2SO_4$:$H_2O$=13:25:12)) was added into an electrochemical working pool. The above-treated materials were used as a working electrode, and a platinum wire electrode was added as a counter electrode, and Ag/AgCl electrode was used as a reference electrode. An electrodeposition was conducted by using a real-time current method at −0.5 V potential condition and with a deposition time of 100 s. There were Pt particles on the carbon fiber paper after deposition. The scanning electron microscopy (SEM) diagram thereof was shown in FIG. 3.

(3) The resultant materials in step (2) were washed with deionized water, so as to wash off residual chloroplatinic acid solution, and were placed to dry. A 10 μl glucose oxidase aqueous solution which contained two active units (i.e. 2U activity) of glucose oxidase was dropped onto surface after platinum deposition treatment in step (2). The materials after dropping were left to dry naturally at room temperature. After drying, there was glucose oxidase on the surface of the materials.

(4) A 10 μL chitosan acetate buffer (at a concentration of 4 mg/ml, pH value of the acetate buffer was about 5.0) was dropped onto surface of the materials which had been dropped with glucose oxidase in step (3). After addition of chitosan solution, the materials were dried naturally. The dried materials were washed with a small amount of deionized water to wash off salt impurities in the film-forming materials and to make film formation more uniform. Materials after washing with deionized water were dried naturally at room temperature. On the surface of the materials after drying, there was a layer of chitosan film, thereby protecting the enzyme molecules from dissolving.

The materials obtained in step (4) could be used as a working electrode for superhydrophobic glucose sensor to detect glucose solution with different concentrations (the concentration of glucose solution were 1 μM, 5 μM, 10 μM, 50 μM, 250 μM, 1 mM, 2 mM, 3 mM, 10 mM and up to 150 mM, respectively, wherein each spacing concentration in a range of 10 mM −150 mM was 5 mM), wherein a platinum wire electrode was used as a counter electrode, and Ag/AgCl electrode was used as the reference electrode, and an electrochemical workstation was used for measurement.

General Detection Methods

Response range was carried out by using a conventional cyclic voltammetry, in which different concentrations of glucose solution were detected, and the scanning range was −0.1V to 0.6V. The concentration value of glucose in the solution was corresponding to an oxidation current value obtained at 0.5V potential sweep, so that the detection was carried out at 0.5V potential.

Response time was measured by using a conventional chronoamperometry, and the potential of working electrode was set at 0.5V, then start scanning. Timing was stopped when the current signal was stable.

Detection Results

Figure 4:
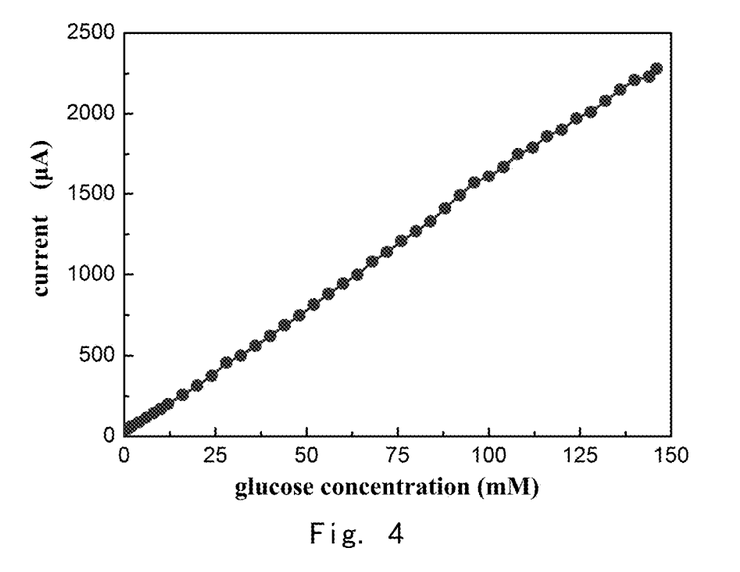
FIG. 4 is a "glucose concentration-current" diagram of a bio-enzyme sensor of the present invention.
Figure 5:
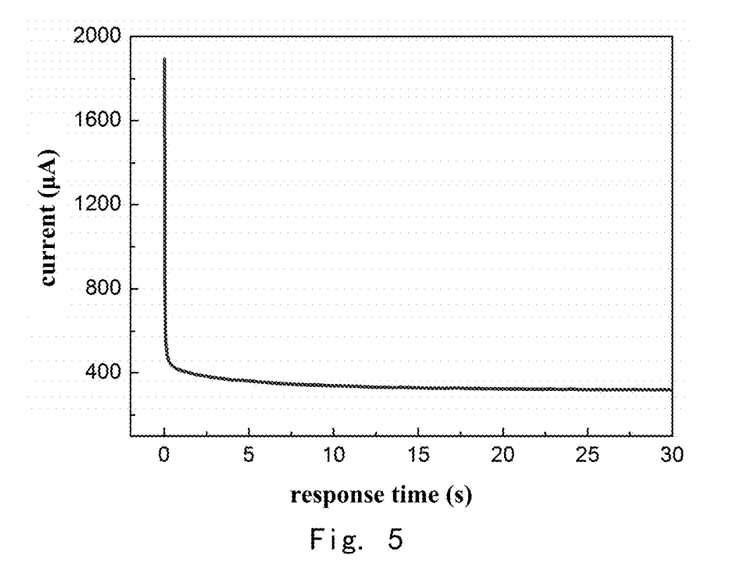
FIG. 5 is a "response time-current" diagram of a bio-enzyme sensor of the present invention.

The glucose sensor obtained in this example had a relatively broad linear response to the concentration of glucose (1 μM-150 mM) as shown in FIG. 4, and had a fast response time (less than 1 second) as shown in FIG. 5.

EXAMPLE 2 Preparation of Superhydrophobic Glucose Sensor (1) The conductive superhydrophobic carbon nanotube/sulfonated polytetrafluoroethylene film (see CN102352547A) (1 $cm^2$) was washed with organic solvent, and was placed to dry naturally.

(2) The superhydrophobic conductive substrate (superhydrophobic materials for short) obtained in step (1) was fixed in the electrochemical working pool, as shown in FIG. 1. Ruthenium trichloride ($RuCl_3$) solution (10 mM) was added into the pool, and the superhydrophobic materials mentioned above was used as a working electrode, and a platinum wire electrode was added as a counter electrode, and Ag/AgCl electrode was used as the reference electrode. An electrodepostion was conducted by using a real-time current method at −0.4 V potential condition with a deposition time of 150 s. There were Ru particles on the surface of the superhydrophobic materials after deposition (3) The resultant superhydrophobic materials obtained in step (2) were washed with deionized water, so as to wash off residual ruthenium trichloride solution, and were placed to dry. A 10 μl glucose oxidase aqueous solution containing 0.1U glucose oxidase was dropped onto the surface after ruthenium deposition treatment in step (2). The superhydrophobic materials after dropping were left to dry naturally at room temperature. After drying, there was glucose oxidase on the surface of the superhydrophobic materials.

(4) A 100 μL Nafion solution (at a concentration of 1%) was dropped onto surface of the superhydrophobic materials which had been dropped with glucose oxidase in step (3). After addition of Nafion solution, the materials were dried naturally. The dried superhydrophobic materials were washed with a small amount of deionized water to wash off salt impurities in the film-forming materials and to make film formation more uniform. Superhydrophobic materials after washing with deionized water were dried naturally at room temperature. On the surface of the superhydrophobic materials after drying, there was a layer of Nafion film, thereby protecting the enzyme molecules from dissolving.

The superhydrophobic materials obtained in step (4) could be used as a working electrode for superhydrophobic glucose sensor. A solution containing glucose was added into the electrochemical pool, and a platinum wire electrode was used as a counter electrode, and Ag/AgCl electrode was used as a reference electrode, and an electrochemical workstation was used for measurement using the same method in Example 1.

The results showed that the glucose sensor of the present example had a broad linear response to a solution with glucose concentration in a range of 1 μM-150 mM, and response time thereof was very short (less than 1 second).

EXAMPLE 3 Preparation of Superhydrophobic Glucose Sensor (1) A copper net (see CN102755951A) was treated with superhydrophobic modification, to form a superhydrophobic conductive substrate (superhydrophobic materials for short).

(2) The superhydrophobic materials obtained in step (1) were fixed in an electrochemical working pool. A chloroplatinic acid solution (10 g/L $H_2PtCl_6$, the concentration ratio of $H_2PtCl_6$:1M $H_2SO_4$:$H_2O$ =13:25:12)) was added into an electrochemical working pool. The above-treated superhydrophobic materials were used as a working electrode, and a platinum wire electrode was added as a counter electrode, and Ag/AgCl electrode was used as a reference electrode. An electrodeposition was conducted by using a real-time current method at −0.5 V potential condition with a deposition time of 50 s. There were Pt particles on the carbon fiber paper after deposition.

(3) The resultant superhydrophobic material in step (2) was washed with deionized water, so as to wash off residual chloroplatinic acid solution, and was placed to dry. A 10 μl glucose oxidase aqueous solution which contained 20U glucose oxidase was dropped onto surface after platinum deposition treatment in step (2). The superhydrophobic materials after dropping were left to dry naturally at room temperature. After drying, there was glucose oxidase on the surface of the superhydrophobic materials.

(4) A 10 μL chitosan acetate buffer (at a concentration of 1 mg/ml, pH value of the acetate buffer was about 5.0) was dropped onto surface of the superhydrophobic materials which had been dropped with glucose oxidase in step (3). After addition of chitosan solution, the materials were dried naturally. The dried superhydrophobic materials were washed with a small amount of deionized water, to wash off salt impurities in the film-forming materials, and to make film formation more uniform. Superhydrophobic materials after washing with deionized water were dried naturally at room temperature. On the surface of the superhydrophobic materials after drying, there was a layer of chitosan film, thereby protecting the enzyme molecules from dissolving.

The superhydrophobic materials obtained in step (4) could be used as a working electrode for superhydrophobic glucose sensor. A solution containing glucose was added into the electrochemical pool, and a platinum wire electrode was used as a counter electrode, and Ag/AgCl electrode was used as a reference electrode, and an electrochemical work station was used for measurement following the same method in Example 1. The results showed that the glucose sensor of the present example had a broad linear response to a solution with glucose concentration in a range of 1 μM-150 mM, and response time thereof was very short (less than 1.5 second).

EXAMPLE 4 Preparation of Superhydrophobic Glucose Sensor (1) The graphene films (see CN103101908A) were treated with superhydrophobic modification, to form a superhydrophobic conductive substrate (superhydrophobic materials for short).

(2) The superhydrophobic materials obtained in step (1) were fixed in an electrochemical working pool. A chloroplatinic acid solution (10 g/L $H_2PtCl_6$, the concentration ratio of $H_2PtCl_6$:1M $H_2SO_4$:$H_2O$=13:25:12)) was added into an electrochemical working pool. The above-treated superhydrophobic materials were used as a working electrode, and a platinum wire electrode was added as a counter electrode, and Ag/AgCl electrode was used as a reference electrode. An electrodeposition was conducted by using a real-time current method at 0 V potential condition and with a deposition time of 400 s. There were Pt particles on the carbon fiber paper after deposition.

(3) The resultant superhydrophobic materials (approximate 1 $cm^2$) in step (2) were washed with deionized water, so as to wash off residual chloroplatinic acid solution, and were placed to dry. A 10 μl glucose oxidase aqueous solution which contained 20U glucose oxidase was dropped onto the surface after platinum deposition treatment in step (2). The superhydrophobic materials after dropping were left to dry naturally at room temperature. After drying, there was glucose oxidase on the surface of the superhydrophobic materials.

(4) A 10 μL chitosan acetate buffer (at a concentration of 250 mg/ml, pH value of the acetate buffer was about 5.0) was dropped onto surface of the superhydrophobic materials which had been dropped with glucose oxidase in step (3). After addition of chitosan solution, the materials were dried naturally. The dried superhydrophobic materials were washed with a small amount of deionized water, to wash off salt impurities in the film-forming materials, and to make film formation more uniform. Superhydrophobic materials after washing with deionized water were dried naturally at room temperature. On the surface of the superhydrophobic materials after drying, there was a layer of chitosan film, thereby protecting the enzyme molecules from dissolving.

The superhydrophobic materials obtained in step (4) could be used as a working electrode for superhydrophobic glucose sensor. A solution containing glucose was added into the electrochemical pool, and a platinum wire electrode was used as a counter electrode, and Ag/AgCl electrode was used as the reference electrode, and an electrochemical workstation was used for measurement following the same method in Example 1.

The results showed that the glucose sensor of the present example had a broad linear response to a solution with glucose concentration in a range of 1 μM-150 mM, and response time thereof was very short (less than 2 second).

EXAMPLE 5 Preparation of Superhydrophobic Glucose Sensor (1) A platinum net (see CN103386396A) was treated with superhydrophobic modification, to form a conductive substrate (superhydrophobic materials for short).

(2) A 10 μl glucose oxidase aqueous solution which contained 15U glucose oxidase was dropped onto surface of the superhydrophobic materials in step (1). The superhydrophobic materials after dropping were left to dry naturally at room temperature. After drying, there was glucose oxidase on the surface of the superhydrophobic materials.

(3) A 10 μL chitosan acetate buffer (at a concentration of 2.5 mg/ml, pH value of the acetate buffer was about 5.0) was dropped onto surface of the superhydrophobic materials which had been dropped with glucose oxidase in step (2). After addition of chitosan solution, the materials were dried naturally again. The dried materials were washed with a small amount of deionized water, to wash off salt impurities in the film-forming material, and to make film formation more uniform. Superhydrophobic materials after washing with deionized water were dried naturally at room temperature again. On the surface of the superhydrophobic materials after drying, there was a layer of chitosan film, thereby protecting the enzyme molecules from dissolving.

The superhydrophobic materials obtain in step (3) were remained in the electrochemical pool, and was used as a working electrode for superhydrophobic glucose sensor. A solution containing glucose was added into the electrochemical pool, and a platinum wire electrode was used as a counter electrode, and Ag/AgCl electrode was used as the reference electrode, and an electrochemical workstation was used for measurement following the same method in Example 1.

The results showed that the glucose sensor of the present embodiment had a broad linear response to a solution with glucose concentration in a range of 1 μM-150 mM, and response time thereof was very short (less than 2 second).

It should be noted that the above description is only preferred embodiments of the present invention, which is not intended to limit the invention. For those skilled in the art, any modifications and improvements etc. within the spirit and principles of the present invention should be included within the scope of the present invention.

The invention claimed is:

1. A bio-enzyme sensor, wherein the bio-enzyme sensor comprises:
   (a) a substrate having superhydrophobic property;
   (b) a catalytic material having a catalytic function for hydrogen peroxide;
   (c) a bio-enzyme capable of reacting with a substance to be detected to generate hydrogen peroxide,
   wherein the catalytic material is distributed on the substrate, or the substrate itself has the catalytic material,
   the bio-enzyme is located on a surface of the substrate and/or the catalytic material,
   a solid phase-liquid phase-gas phase coexistence form is formed at a contact interface when the sensor is in contact with a solution containing the substance to be detected,
   the substrate includes
   a metal material or
   a high molecular porous material,
   the metal material includes foamed nickel, foamed copper, foamed titanium, foamed aluminum and iron net, foamed copper mesh, foamed aluminum net, aluminum and iron mesh, copper mesh, or aluminum mesh, or a combination thereof, and
   the high molecular porous material includes a polypyridine membrane.

2. The bio-enzyme sensor according to claim 1, wherein at least a portion of the bio-enzyme and at least a portion of the catalytic material are in contact with each other.

3. The bio-enzyme sensor according to claim 1, wherein the solid phase-liquid phase-gas phase coexisting form includes the bio-enzyme sensor as a solid phase, and the solution as a liquid phase, and air or atmospheric as a gas phase.

4. The bio-enzyme sensor according to claim 1, wherein the bio-enzyme sensor is selected from the group consisting of:
   (S1) the bio-enzyme sensor comprises: the substrate having superhydrophobic property; the bio-enzyme; and the catalytic material distributed on the substrate,
   wherein the catalytic material has a catalytic function for hydrogen peroxide, and the bio-enzyme is capable of reacting with the substance to be detected to generate hydrogen peroxide;
   (S2) the bio-enzyme sensor comprises the substrate that is a conductive substrate having superhydrophobic property,
   wherein the substrate itself comprises a catalytic material having a catalytic function for hydrogen peroxide, and the bio-enzyme capable of reacting with the substance to be detected to generate hydrogen peroxide;
   (S3) the bio-enzyme sensor comprises: the substrate that is a conductive substrate having a superhydrophobic structure; the bio-enzyme; and the catalytic material,
   wherein the bio-enzyme is capable of reacting with the substance to be detected to generate hydrogen peroxide and the catalytic material has a catalytic function for hydrogen peroxide, and
   when a surface of the superhydrophobic structure is applied with a selected liquid system, the bio-enzyme and the catalytic material are at least distributed on an interface of the liquid phase covering the superhydrophobic structure, and an oxygen-containing gas phase is present within the superhydrophobic structure, thus forming the solid-liquid-gas three-phase coexisting form; and
   (S4) the bio-enzyme sensor comprises the substrate that is a conductive substrate having a superhydrophobic structure,
   wherein the superhydrophobic structure is formed from a material comprising: a catalytic material having a catalytic function for hydrogen peroxide; and the bio-enzyme capable of reacting with the substance to be detected to generate hydrogen peroxide, and
   when a surface of the superhydrophobic structure is applied with a selected liquid system, the bio-enzyme and the catalytic material are at least distributed on an interface of the liquid phase covering the superhydrophobic structure, and an oxygen-containing gas phase is present within the superhydrophobic structure, thus forming the solid-liquid-gas three-phase coexisting form.

5. The bio-enzyme sensor according to claim 1, wherein the bio-enzyme sensor has one or more characteristics selected from the group consisting of:
   (F1) when the substance to be detected has a concentration range of 1 µM-500 mM, a measuring current of the bio-enzyme sensor is linear or nearly linear;
   (F2) a response time of the bio-enzyme sensor is ≤5 seconds;
   (F3) operation of the sensor is not influenced by oxygen content in the solution containing the substance to be detected.

6. The bio-enzyme sensor according to claim 5, wherein the response time of the sensor is ≤1 second.

7. The bio-enzyme sensor according to claim 1, wherein the catalytic material comprises an inorganic material and/or an organic material;
   the inorganic material includes one or more selected from the group consisting of carbon material, metal, and metal oxide;
   the metal includes platinum, rhodium, ruthenium, gold, cobalt, iron, or nickel;
   the metal oxide includes one oxide or a combination of two or more oxides, wherein the oxide is an oxide of rhodium, ruthenium, cobalt, iron, or nickel; and
   the organic material includes biological material or metal organic complex, wherein the biological material comprises cytochrome C, hydrogen peroxide oxidase, or Prussian blue.

8. The bio-enzyme sensor according to claim 1, wherein the catalytic material comprises metal and/or metal oxide nanoparticle.

9. The bio-enzyme sensor according to claim 1, wherein the bio-enzyme includes glycerol kinase, α-glycerophosphate oxidase, cholesterol esterase, cholesterol dehydrogenase, cholesterol oxidase, glucose oxidase, glucose dehydrogenase, lactate dehydrogenase, malic dehydrogenase, bilirubin oxidase, ascorbic acid oxidase, peroxidase, uricase, collagenase, hyaluronic acid enzyme, proteases, proteolytic enzyme, or a combination thereof.

10. The bio-enzyme sensor according to claim 1, wherein the bio-enzyme sensor further comprises a protective film, wherein the protective film is at least to protect the bio-enzyme and fix the bio-enzyme on the surface of the substrate.

11. The bio-enzyme sensor according to claim 10, wherein the protective film prevents the bio-enzyme from permeating through the protective film, but allows the following materials to permeate through: a solvent molecule forming a selected liquid system and the substance to be detected.

12. The bio-enzyme sensor according to claim 10, wherein the protective film is formed from a material selected from the group consisting of chitosan, perfluorosulfonic acid proton membrane, and a combination thereof.

13. The bio-enzyme sensor according to claim 1, wherein the bio-enzyme sensor has one or more characteristics selected from the group consisting of:
(F1) when the substance to be detected has a concentration range of 1 μM-150 mM, a measuring current of the bio-enzyme sensor is linear or nearly linear; and
(F2) a response time of the bio-enzyme sensor is ≤2 seconds.

14. The bio-enzyme sensor according to claim 1, wherein the bio-enzyme is glucose oxidase and the substance is glucose, the bio-enzyme sensor has a linear response to a solution having a glucose concentration in a range of 1 μM-150 mM with a response time of less than 2 seconds.

15. A method for preparing a bio-enzyme sensor, comprising:
(i) providing a substrate having superhydrophobic property, wherein a catalytic material is distributed on the substrate, or the substrate itself has the catalytic material, wherein the catalytic material has a catalytic function for hydrogen peroxide; and
(ii) loading a bio-enzyme on the substrate of step (i), thereby forming the bio-enzyme sensor, wherein the bio-enzyme is capable of reacting with a substance to be detected to generate hydrogen peroxide,
wherein, in step (i), firstly providing the substrate wherein the surface of the substrate has a superhydrophobic structure or superhydrophobic property, and then loading the catalytic material on the substrate;
in step (ii), the loading step comprises the following steps:
applying a solution containing the bio-enzyme to the substrate and drying, so that the bio-enzyme is attached to a surface of the substrate;
the catalytic material comprises inorganic materials and/or organic materials;
the bio-enzyme includes one or more enzymes selected from the group consisting of glycerol kinase, α-glycerophosphate oxidase, cholesterol esterase, cholesterol dehydrogenase, cholesterol oxidase, glucose oxidase, glucose dehydrogenase, lactate dehydrogenase, malic dehydrogenase, bilirubin oxidase, ascorbic acid oxidase, peroxidase, uricase, collagenase, hyaluronic acid enzyme, proteases, and proteolytic enzyme;
the substrate is a conductive substrate whose surface is modified by a material having low surface energy; and
the bio-enzyme sensor comprises:
(a) a substrate having superhydrophobic property;
(b) a catalytic material having a catalytic function for hydrogen peroxide;
(c) a bio-enzyme capable of reacting with a substance to be detected to generate hydrogen peroxide,
wherein the catalytic material is distributed on the substrate, or the substrate itself has the catalytic material,
the bio-enzyme is located on a surface of the substrate and/or the catalytic material,
a solid phase-liquid phase-gas phase coexistence form is formed at a contact interface when the sensor is in contact with a solution containing the substance to be detected.

16. The method according to claim 15, wherein the method further comprises:
applying a film-forming material on the substrate loaded with the bio-enzyme and drying, thereby forming a protective film on the substrate.

\* \* \* \* \*